(12) United States Patent
Grundei et al.

(10) Patent No.: US 6,319,255 B1
(45) Date of Patent: Nov. 20, 2001

(54) PROPHYLACTIC IMPLANT AGAINST FRACTURE OF OSTEOPOROSIS-AFFECTED BONE SEGMENTS

(75) Inventors: Hans Grundei, Lübeck (DE); Wolfram Thomas, Rome (IT)

(73) Assignee: ESKA Implants GmbH & Co., Lubeck (DE)

( * ) Notice: Subject to any disclaimer, the term of this patent is extended or adjusted under 35 U.S.C. 154(b) by 0 days.

(21) Appl. No.: 09/336,023

(22) Filed: Jun. 18, 1999

Related U.S. Application Data (63) Continuation of application No. PCT/EP97/06568, filed on Nov. 25, 1997.

(30) Foreign Application Priority Data

Dec. 18, 1996 (DE) .............................. 196 52 608

(51) Int. Cl.⁷ .................................................. A61B 17/68
(52) U.S. Cl. .................. 606/76; 606/60; 606/61; 606/62; 606/63; 606/67; 606/68; 606/72; 623/16.11; 623/20.36
(58) Field of Search ................. 606/62, 60, 61, 606/65, 66, 67, 68, 72, 76, 77, 63; 623/16.11, 17.11, 17.16, 20.36

(56) References Cited

U.S. PATENT DOCUMENTS

| | | |
|---|---|---|
| 2,537,070 | 9/1951 | Longfellow . |
| 4,195,367 | 4/1980 | Kraus . |
| 4,328,593 | * 5/1982 | Sutter et al. . |
| 4,932,973 | 6/1990 | Gendler . |
| 5,147,402 | * 9/1992 | Bohler et al. . |
| 5,433,750 | * 7/1995 | Gradinger et al. ................. 623/16 |
| 5,441,536 | * 8/1995 | Aoki et al. ..................... 427/2.27 |
| 5,549,704 | * 8/1996 | Sutter . |
| 5,563,124 | 10/1996 | Damien et al. . |
| 5,593,409 | * 1/1997 | Michelson ........................ 606/61 |

FOREIGN PATENT DOCUMENTS

| | | |
|---|---|---|
| 34 14 992 A1 | 10/1985 | (DE) . |
| 39 37 361 A1 | 5/1991 | (DE) . |
| 42 08 247 C1 | 10/1993 | (DE) . |
| 195 08 224 A1 | 9/1995 | (DE) . |
| 295 09 739 U1 | 11/1996 | (DE) . |
| 0 636 346 A1 | 2/1995 | (EP) . |
| WO 96/39974 | 12/1996 | (WO) . |

\* cited by examiner

*Primary Examiner*—David O. Reip
(74) *Attorney, Agent, or Firm*—Akin, Gump, Strauss, Hauer & Feld, L.L.P.

(57) ABSTRACT

A prophylactic implant is provided for protecting osteoporosis-affected bone segments against fractures, in particular the neck of the femur, the vertebral column and the wrist. According to a proposed solution, the implant comprises a thin-walled hollow reinforcing body (1) having such a large number of passages (2) in its outer wall (3) that the ratio of the total area of the passages (2) to the total surface area is at least 1:2.

20 Claims, 7 Drawing Sheets

PROPHYLACTIC IMPLANT AGAINST FRACTURE OF OSTEOPOROSIS-AFFECTED BONE SEGMENTS

CROSS REFERENCE TO RELATED APPLICATION

This application is a continuation of International Application PCT/EP97/06568, filed Nov. 25, 1997, the disclosure of which is incorporated herein by reference.

BACKGROUND OF THE INVENTION

The invention relates to a prophylactic implant against fractures of osteoporosis-affected bone segments.

There are millions of osteoporotic persons in Germany alone, who most frequently have other diseases of the locomotor system.

Osteoporosis is accompanied by a loss of the bone mass, which exceeds the natural age-related bone disintegration. In addition, the quality of the microstructure of the bone tissue degrades. The loss of the bone mass, bone structure and function leads to clinical symptoms with lasting infirmities and fractures. Femoral neck fractures, fractures of the vertebral column and of the wrist are particularly widespread.

In the case of osteoporotic fractures of the femoral neck, the treatment at the present time mainly involves the complete resection of the femur and natural acetabulum, as well as the implantation of a complete artificial hip joint system. These systems are presently quite well developed, but this intervention should nevertheless be regarded as a severe intervention as has always been the case. In addition, as before, particularly critical is the long-term stability of the implant in the patient body. Influences on this have been, for example, the type of implant (with or without cementing), age and constitution of the patient, as well as many other parameters. Apart from this, it would be desirable if the total resection of bone segments could be deferred as long as possible, even in osteoporotic patients, or would become completely superfluous.

Starting points for an early diagnosis of the anticipated trauma or the fracture of the affected bone segment follow from modern radiological examinations. Signs of the osteoporosis-induced alterations in the bone structure can be clearly determined radiologically, and interestingly, the anticipated fracture can be predicted with astonishingly high accuracy within a period up to one year. This knowledge gives the opportunity and the chance to intervene therapeutically before the fracture occurs and to stop or retard the osteoporosis.

An implant, which can also be used for prophylactic purposes, is known from U.S. Pat. No. 2,537,070. The implant has a thin-walled reinforcing body with a plurality of passages in its outer wall. Pulverized bone material is pressed into the reinforcing body during the implantation. A contact between the spongiosa surrounding the implant and the pulverized bone material is allowed by the openings in the wall of the implant. A fixation should be achieved thereby through absorption of moisture through the surrounding bone structure.

From German published patent application DE-A-195 08 224 an implant is known which can be inserted as a prophylactic implant against fractures of osteoporosis-affected bone segments. This implant consists of a solid implant core forming a reinforcing core for the bone segment. The surface of the core member is coated with a surface layer of a dense or porous biocompatible material.

The described implants are thought, in the first place, to repair defects which have already occurred, i.e., osteoporotic bones threatened by a fracture can possibly be protected beforehand. The above-mentioned early diagnosis of an anticipated trauma or the fracture still plays no role for the known implants.

SUMMARY OF THE INVENTION

In view of this background, it is an object of the present invention to provide an implant against fractures of osteoporosis-affected bone segments, which in a particular manner is suited for a prophylactic use.

According to the first embodiment, the prophylactic implant has a thin-walled hollow reinforcing body with such a large number of passages in its outer wall, that the ratio of the total area of the passages (i.e., the area of the openings of the passages on the outer wall) to the total surface area (i.e., the area of the outer wall including openings therein) is at least 1:2.

The reinforcing body can in the broadest sense also be designated as a reinforcing sleeve. It is essential that its interior allow the possibility of the bone material growing through the passages into its interior, or in another embodiment, bioresorbable material in the interior of the reinforcing body is gradually resorbed and replaced by bone material growing in from outside. The reinforcing body according to the invention thereby forms a place holder or seat for after-growing sound bone material, in place of the previously-removed osteoporotic bone material.

As far as the operation is concerned, the osteoporosis-affected bone segment is milled out or drilled out, and a reinforcing body according to the invention, form-fitted to the resulting bore, is inserted into the bone segment being treated. The thus treated bone segment is then closed up again in a conventional manner. This operation provides a reinforcing body, which is initially hollow, to remain in the interior of the bone segment being treated. On account of the local conditions and in case of a rough surface of the reinforcing body, the bone material grows from outside into the interior of the reinforcing body and, indeed, until the body is completely filled with natural spongiosa. This spongiosa no longer has to adhere to the defective osteoporosis-affected bone material; the structure and the stability of the affected bone are thereby again produced.

Alternatively, the operating surgeon can proceed by filling the interior of the reinforcing body with a healing enhancement agent, wherein here particularly a hydroxylapatite or an alpha-tricalcium phosphate ceramic is intended. This material can optionally be pressed into the interior of the reinforcing body as a plug by means of an appropriate tool. The material is bioresorbable, so that after a resorption of the material in the course of time, the natural bone material grows into the interior of the reinforcing body.

In addition to the main effect, that an osteoporosis-induced fracture of the bone segment can be delayed or completely avoided, it is also to be cited that the burden on the patient during the operation is substantially reduced in comparison with that of the implantation of a complete replacement implant, since the prophylactic implant according to the invention can be implanted in the course of an ambulatory intervention with only a local anesthesia. If the prophylactic implant according to the invention is thus put in place within the forecast time frame of up to one year before a fracture of the affected bone segment occurs, there is a high probability of a decided unburdening of the patient from the otherwise total operative intervention becoming necessary, since the joint itself is generally still intact at the time of the precautionary examination.

According to a first preferred embodiment, the reinforcing body is made of a biocompatible metal, and it is provided with an open-mesh, three-dimensional spatial network structure on sections of its surface. The above-mentioned spatial network structure serves to allow the surrounding bone material to grow through this structure and thus exercises a restraining effect against movement of the implant from the milled out bore in the bone segment being treated. In the extreme case, i.e., with a very large ratio of the total area of the passages to the total surface area, the reinforcing body can be a sort of metal network. The three-dimensional spatial network structure can then be provided, depending on the place of implantation, at chosen points of the surface of the implant.

According to another preferred embodiment, it is provided that the reinforcing body is made of a biocompatible dimensionally stable, yet still elastic, plastic, wherein the reinforcing body is deformable by means of a built-in mechanism by application of a pulling force (tension). The deformation of the reinforcing body, which is imparted as required, has the purpose of holding it in place, i.e., to prevent a displacement from the zone of implantation. The deformation is possible since the implant body is made of an elastic plastic in this embodiment described above.

In a special construction of the prophylactic implant of the invention as a femoral neck implant, according to a preferred embodiment, it is provided that the reinforcing body is made as a substantially cylindrical sleeve, which is closed distally with a convex head member and which is proximally closable with a closing piece. Also possible is a conical construction of the sleeve tapering in the direction toward the articular head of the hip joint.

The proximally installed closing piece serves for closing the sleeve after the optionally undertaken filling of the interior of the sleeve with, for example, hydroxylapatite, alpha-tricalcium phosphate ceramic, or a mixture thereof with the previously milled-out spongiosa (see above). For example, the closing piece can be screwed by means of a screw thread in a threaded bore in the sleeve. Operatively, it can be expedient, before the closing of the sleeve, to drive a sort of plug through the threaded bore in the sleeve to compress the material found in the interior, so that it advances to the bone wall at all points of the bone canal, artificially created by the passages in the outer wall of the sleeve, so that the resorption process can begin immediately.

If the sleeve is made of metal in this embodiment, it is preferred that the convex head member be provided with the spatial network structure at least in certain locations, in order to allow the surrounding bone material to grow through the structure, as described above, for long-term fixation of the implant in situ. Also, the proximal closing piece can be provided with the spatial network structure at least in certain locations, and exactly for the same purpose.

In the construction of the implant as a femoral neck implant made of biocompatible plastic in accordance an advantageous embodiment, a threaded shaft is provided in the interior of the sleeve between the head member and the closing piece and connected with these two parts, by means of which the pulling force necessary for the compression is generatable by rotation of the threaded shaft. More specifically, during the operation, after the insertion of the sleeve into the bone canal, the surgeon sets the threaded shaft into rotation by means of a tool, for example a screwdriver, so that this has the effect of pulling the head member in the direction toward the closing piece, whereby owing to the elasticity of the plastic, the sleeve expands slightly outwardly and so achieves the restraining action.

Alternatively, it can be provided for this that a pulling cord is tensioned in the interior of the sleeve between the head member and the closing piece, the pulling cord being further tensionable by the surgeon from outside, for example by use of a screwdriver, in order to be able to generate the pulling force applied for deformation of the sleeve.

The pulling cord can be attached for this purpose to the head member by means of a tension plate, whereas the counterpiece at the opposite end engages with a threaded bore in the closing piece.

According to yet another advantageous development, it can be provided in all the above-described embodiments, that the outer wall is coated with an agent that is resorbable by the human body. This enhances the acceptance of the implant in the bones and accelerates the resorption, i.e., ultimately the embedding and incorporation of the bone material. As agents for this purpose, it is preferred to use again hydroxylapatite or an alpha-tricalcium phosphate ceramic.

According to a first alternative proposed solution, it is provided that the prophylactic implant is made of a solid implant core forming a reinforcing core for the bone segment, whose surface is provided with an open-mesh, three-dimensional spatial network structure at least in certain areas. The latter can be a multi-layer application to achieve a maximum possible spatial depth, through which the after-growing sound bone material can grow. In this case, the operation proceeds again by cleaning out the osteoporosis-affected bones by milling or boring and inserting the implant in place of the spongiosa which was altered by osteoporosis. The beneficial effect is also achieved here by the fact that sound bone material grows anew and so stabilizes the bone structure.

According to a second alternative proposed solution, it is provided that the implant has a hollow tube, whose outer wall is formed by an open-mesh, three-dimensional spatial network structure. By this spatial network structure, as described with reference to the first proposed solution, the bone material can grow from outside into the interior of the sleeve. Of course, with the present proposal no additional preparation of a mechanism and no special external structure whatsoever is required, in order to prevent a displacement of the implant from the bone segment, since specifically the open-mesh, three-dimensional spatial network structure, which simultaneously forms the sleeve wall, is grown through and around by bone and thus exercises the restraining function. The above-described embodiment can be still further advantageously improved in that the hollow pipe forms a sleeve, which is closable from the proximal end with a closing piece, wherein the closing piece itself is likewise made of an open-mesh, three-dimensional spatial network structure. This embodiment allows the interior of the sleeve, similarly to the first proposed solution, to be optionally filled with a healing enhancement agent (hydroxylapatite, alpha-tricalcium phosphate ceramic, etc.) in order to accelerate the healing process. In this case, the spatial network structure of the closing piece likewise serves for the through growth of bone material.

This proposed solution is also based on the philosophy according to which a fracture of the osteoporosis-affected bone segment is thereby to be deferred or to be prevented, in that first the osteoporosis-affected bone is milled out and in place of the diseased spongiosa the implant according to the invention is inserted, which is grown through by healthy after growing bone material, whereby finally the stability of the whole bone is recovered or at least substantially enhanced.

According to a further improvement of the implant, in which the reinforcing body is hollow, it is provided that an electric coil, which is externally energizable, is arranged in the reinforcing body on a magnetic core centrally arranged in the reinforcing body.

The present invention takes advantage of the so-called magnetically induced electrical stimulation in orthopedics, as extensively described in the pertinent literature of this field. Reference can be made, for example, to the paper of W. Kraus, "Magnetic Field Therapy and Magnetically Induced Electrostimulation in Orthopedics," *DE-Z-Orthopäde* 13:78–92 (1984).

The coil arranged on the magnetic core is considered in this configuration as the secondary winding of a transformer, whose primary winding is placed externally on the patient. A low-frequency alternating current in the primary winding generates a likewise low-frequency voltage at the terminals of the secondary winding on the magnetic core. An electric current then flows in the secondary winding across the filler material in the interior of the reinforcing body, to stimulate the bone growth in a known manner.

As a result, the reinforcing body is grown through more rapidly by natural spongiosa, whereby the structure and stability of the affected bone are recovered substantially faster.

According to a further advantageous improvement, it can be provided that the magnetic core can be constructed as a threaded shaft, which serves the purpose, according to the main application, to deform the cylindrical sleeve of the reinforcing body, which is made of plastic in this case, by rotating the threaded shaft, in order to restrain a tendency of the implant to drift within the bone canal.

In accordance with a still further advantageous embodiment, it is provided that the head member has an extension, which protrudes into the interior of the reinforcing body and has a recess which secures the centered position of the magnetic core. The head member and the extension can, for example and preferably, be made of an appropriate ceramic material. If the tip of the magnetic core is constructed, for example, with a conical shape, then the recess is preferably provided in the ceramic material with a complementary shape.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

In the figures, like parts are respectively provided with the same reference numerals.

DETAILED DESCRIPTION OF THE INVENTION

Figure 1:
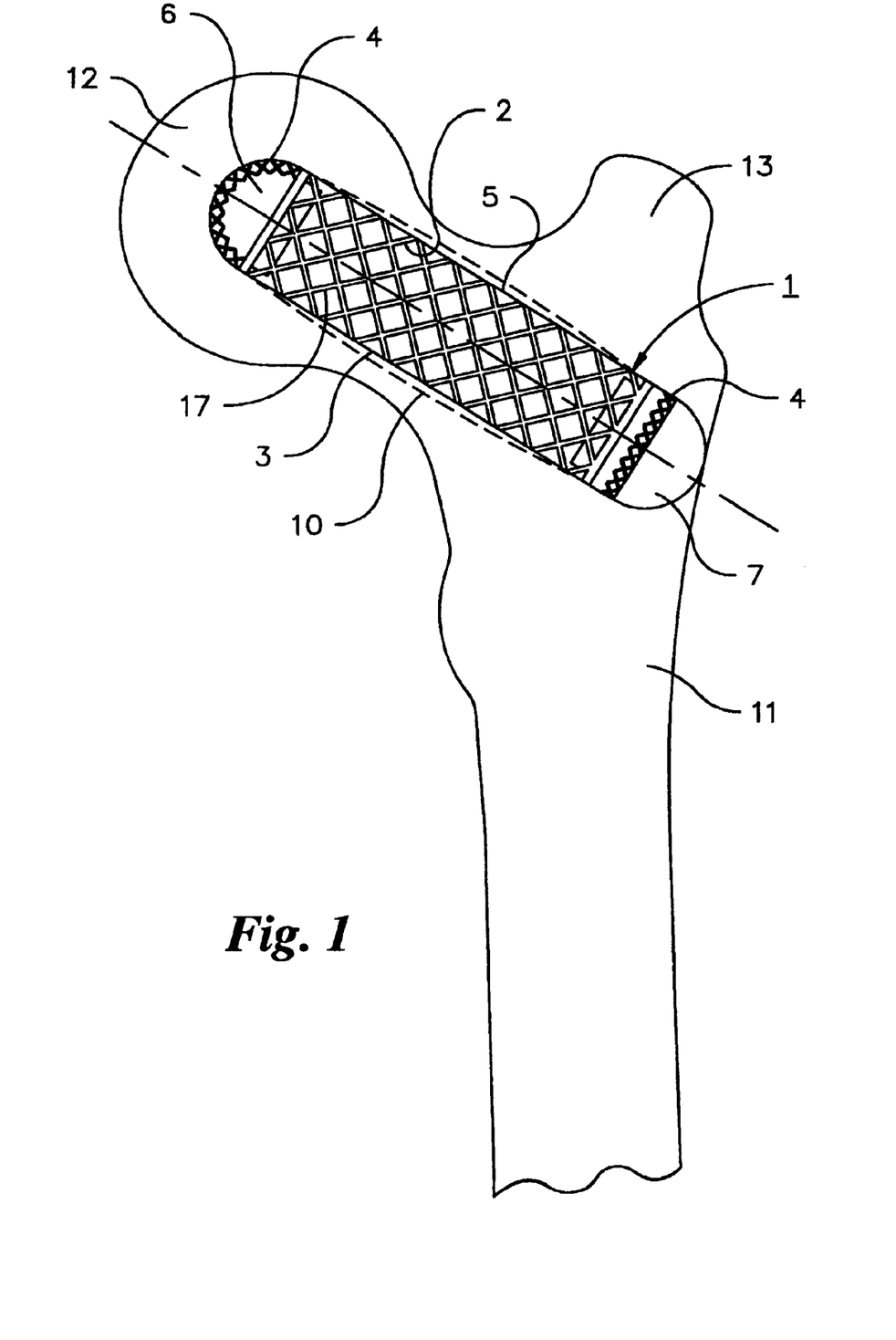
FIG. 1 is a schematic view of the implant position of an implant in the femur according to a first embodiment.

FIG. 1 illustrates the installation position of the reinforcing body 1 in the femur 11 of a patient, more specifically in the femoral neck. The reinforcing body 1 is shown here as a femoral neck implant, which substantially consists of a cylindrical sleeve 5. The sleeve 5 is installed in a bone canal made in the femoral neck under the trochanter major 13 and forms there a quasi seat for newly growing sound bone material. For this purpose, the sleeve 5 has passages 2 in the outer wall 3. In the implant shown, the ratio of the total area of the passages 2 to the total surface area of the implant is substantially greater than 1:2. The implant shown here is constructed of a metallic network having network links (meshes) 17. Distally, i.e., in the direction looking toward the articular head 12, the cylindrical sleeve 5 is closed with a convex head member 6. The convex head member 6 shows an open-mesh, three-dimensional spatial network structure 4 on its surface in certain areas, through which bone material grows after some time, in order to prevent the sleeve 5 from slipping or drifting from the implantation position.

Proximally, that is in the area of introducing the boring or the bone canal in the femur 11, the sleeve 5 is presently closed with a closing piece 7, which, as the head member 6, has an open-mesh, three-dimensional spatial network structure in certain areas, which again is grown through by bone material for securing the implantation position.

Here, the outer wall 3 of the sleeve 5 is coated with a bioresorbable agent 10, which, for example, is hydroxylapatite or is made of an alpha-tricalcium phosphate ceramic.

Figure 2:
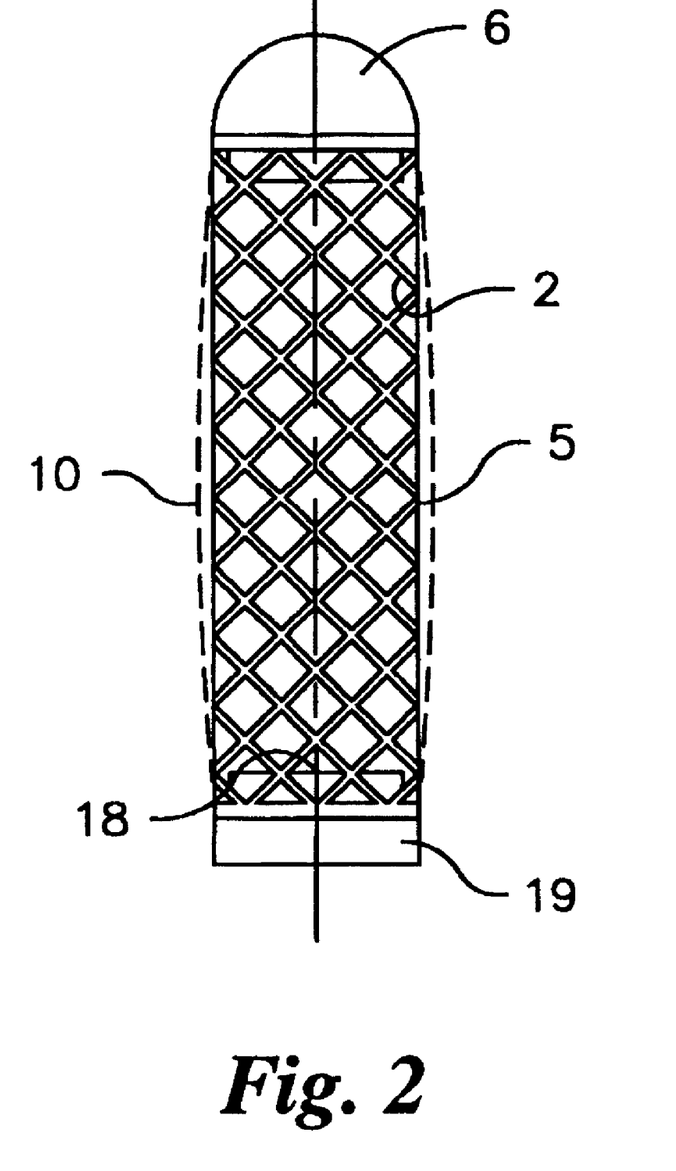
FIG. 2 shows the sleeve part of the implant of FIG. 1 without closing piece.

FIG. 2 shows the sleeve part 5 of the implant from FIG. 1, but not in the implanted state. Here, reference is particularly made to the through bore 18 in the base 19 of the sleeve 5. The through bore 18 is preferably a threaded bore, into which the closing piece 7 (FIG. 1) can be screwed. Before this is undertaken, however, the surgeon can, according to his choice, still guide a sort of pestle through the through bore 18, insofar as a filler material is to be filled into the interior of the sleeve. This filler material can consist of hydroxylapatite, an alpha-tricalcium phosphate ceramic, or a mixture of the two, or one of them with parts of the spongiosa removed by milling. The pestle to be inserted through the through bore 18 compresses this mass in the interior of the sleeve 5, so that this material is pressed through the passages 2 against the wall of the bone canal. A healing enhancement agent can be used here, since the natural bone material proper immediately stands in contact with the bioresorbable material.

Figure 3:
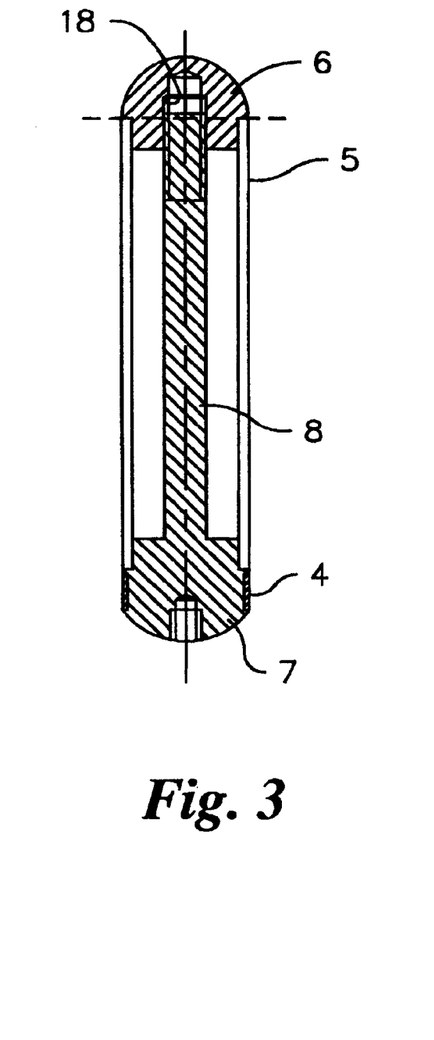
FIG. 3 shows another embodiment of the implant made of plastic.

FIG. 3 shows a section through a femoral neck implant in the form of a cylindrical sleeve 5 made of plastic, which is again closed distally with the convex head member 6 and proximally with a closing piece 7. In order to restrain the implant from the tendency to drift within the bone canal, the closing piece 7 here is provided with a threaded shaft 8, which engages in a threaded bore 18 in the head member 6. By rotating the closing piece 7, the surgeon can now adjust the pulling force, with which the head member 6 is pulled toward the closing piece 7, whereby the elastic plastic material of the sleeve 5 yields, and the implant thus takes on a slightly bulbous outside shape. The surrounding bone area is thereby compacted, whereby the chances for healing under protection of the anti-drifting effect are enhanced.

In this embodiment only a small area of the closing piece 7 is covered with the open-mesh, three-dimensional spatial network structure, in order to prevent micro-displacements of this part by through growing of the structure with bone material.

Figure 4:
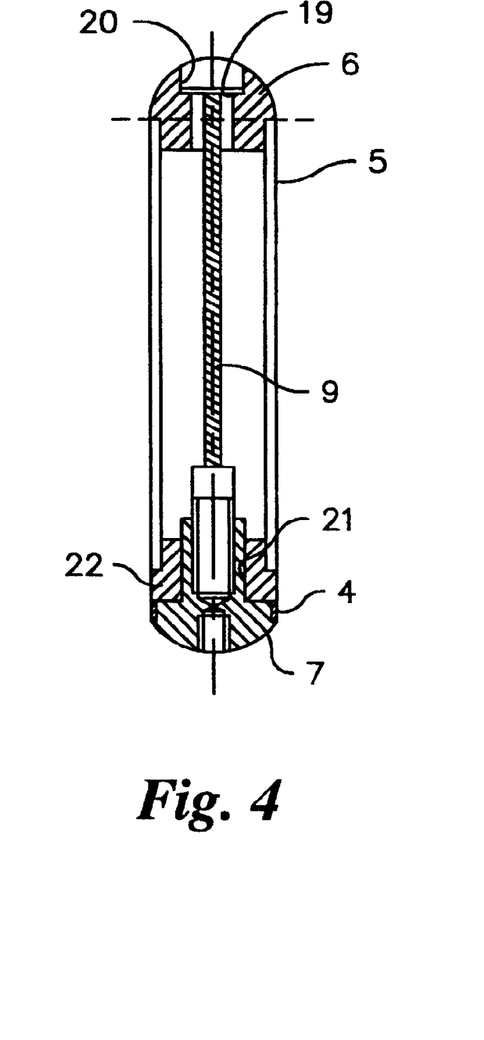
FIG. 4 shows a still further embodiment of the implant made of plastic.

FIG. 4 shows likewise a section through a further embodiment. Here, a pulling cord 9 is tensioned between the head member 6 and the closing piece 7, for which purpose a tension plate 19, to which the pulling cord 9 is attached, lies in a bore 20. The closing piece 7 engages with a threaded shaft 21 through a threaded bushing 22, which is mounted in the interior and on the base of the sleeve 5 and has a matching threaded bore. When the closing piece 7 is rotated, the pulling cord 9, which is anchored in the threaded shaft 21, is now further tensioned, whereby, as explained in connection with the embodiment according to FIG. 3, the sleeve is caused to expand, whereby the implant is fixed in the bone canal. Also in this embodiment, the closing piece 7 carries in small sections an open-mesh, three-dimensional spatial network structure, which secures the through growing with bone material for fixing the closing piece 7 in the bone.

Figure 5:
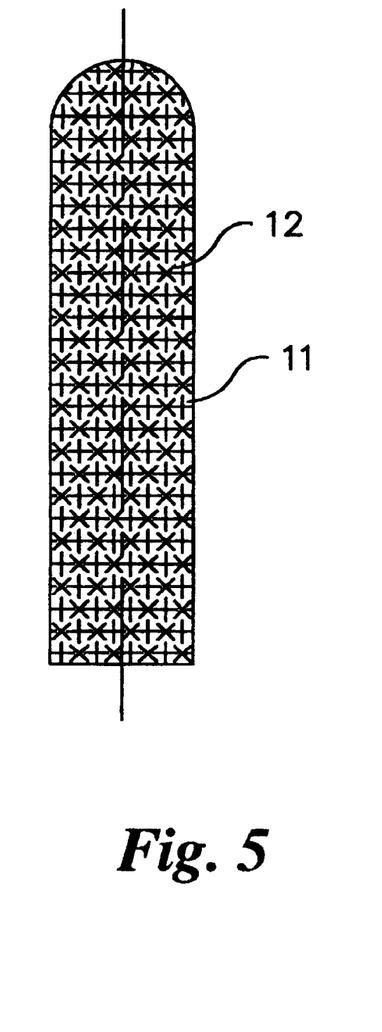
FIG. 5 is the view of an implant according to the first alternative proposed solution.

FIG. 5 shows an implant according to the invention, according to the first alternative proposed solution. Shown is the construction of the implant again as a femoral neck implant. In this case, this consists of a solid implant core 11 whose surface here is completely provided with an open-mesh, three-dimensional spatial network structure 12. Here, it is not a case of a hollow implant, which is completely filled with newly growing spongiosa in the course of time, but an implant that represents a sort of core reinforcement for the osteoporosis-affected bones. The spatial network structure 12 in this case can be built up in several layers with the goal that as much as possible of the newly growing sound bone material grows through it.

Figure 6:
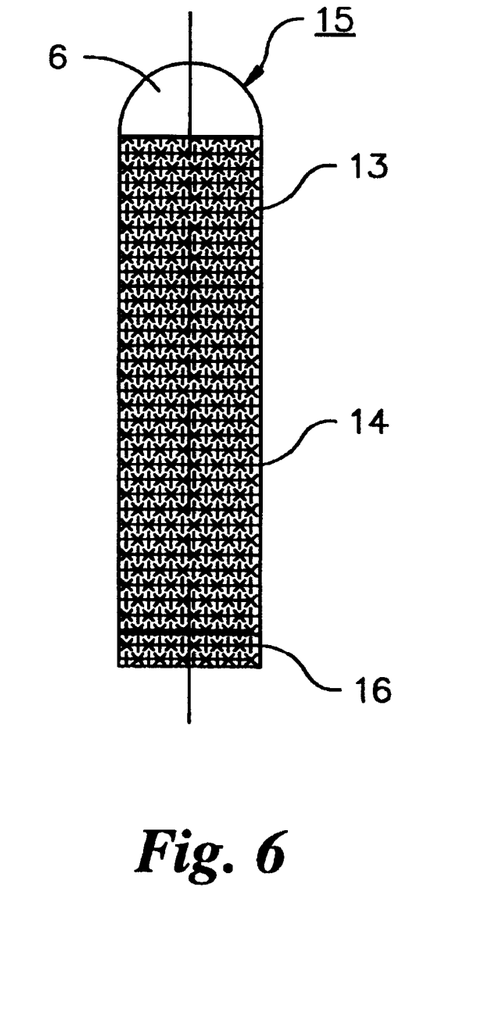
FIG. 6 is the view of an implant according to the second alternative proposed solution.

FIG. 6 shows a second alternative embodiment of the invention. It also depicts a femoral neck implant, which in this case is constructed as a hollow tube 13. The outer wall of the hollow tube 13 is constructed from an open-mesh, three-dimensional spatial network structure 14, through which again the bone material should grow. The hollow tube 13, which forms a sleeve 15, is closed distally with a head member 6, as already described further above.

A closing piece 16 is here arranged proximally, by which the sleeve 15 can be closed.

According to this embodiment, no measures at all are needed in order to prevent a drift of the implant from the bone canal formed in the femoral neck, since the spatial network structure 14 itself assures the positional stability.

The remaining effects of this embodiment are comparable to those of the implant according to FIGS. 1 and 2, for which reason reference is made thereto.

Figure 7:
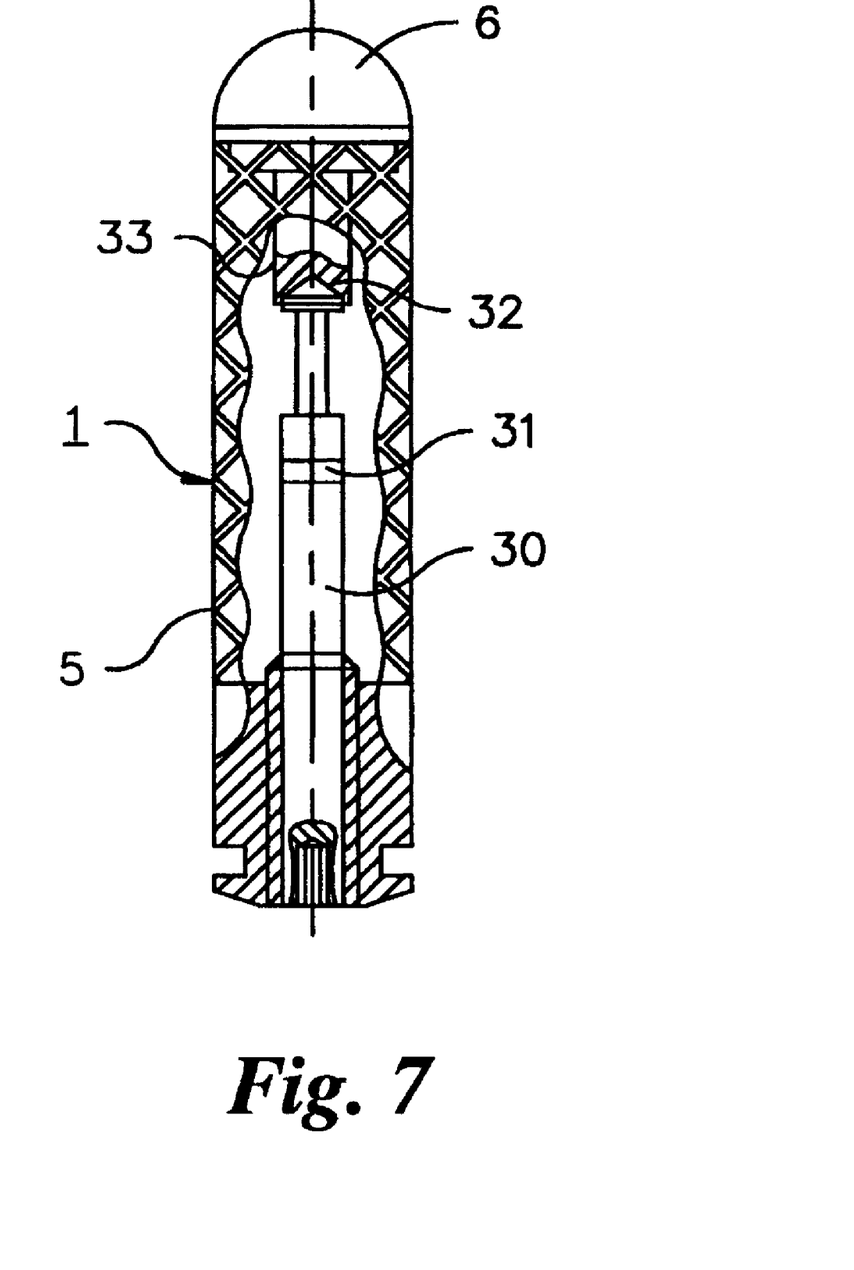
FIG. 7 is the view of the implant according to the further improvement, partially broken away.

As shown schematically in FIG. 7, the reinforcing body 1 is here essentially a hollow cylindrical sleeve 5. In addition, a magnetic core 30 is positioned centrally in the interior of the sleeve 5. The magnetic core 30 carries a coil 31, which is the secondary winding of a transformer, which is formed from the coil 31 and a primary winding or coil (not shown), which is applied externally on the patient body, and through which a low-frequency alternating current of about 0.2 to 20 Hz is conducted, in order to initiate the treatment. This alternating current in the primary circuit induces a current in the secondary circuit, more specifically in the coil 31 and in the filler material located between the two terminals of the coil in the interior of the sleeve 5.

The head member 6 of the sleeve 5 has an extension 33 protruding into the interior of the reinforcing body 1 and having at its foward end a recess 32 complementary in shape to the tip of the magnetic core 30. The head member 6 is preferably made of a biocompatible ceramic.

Figure 8:
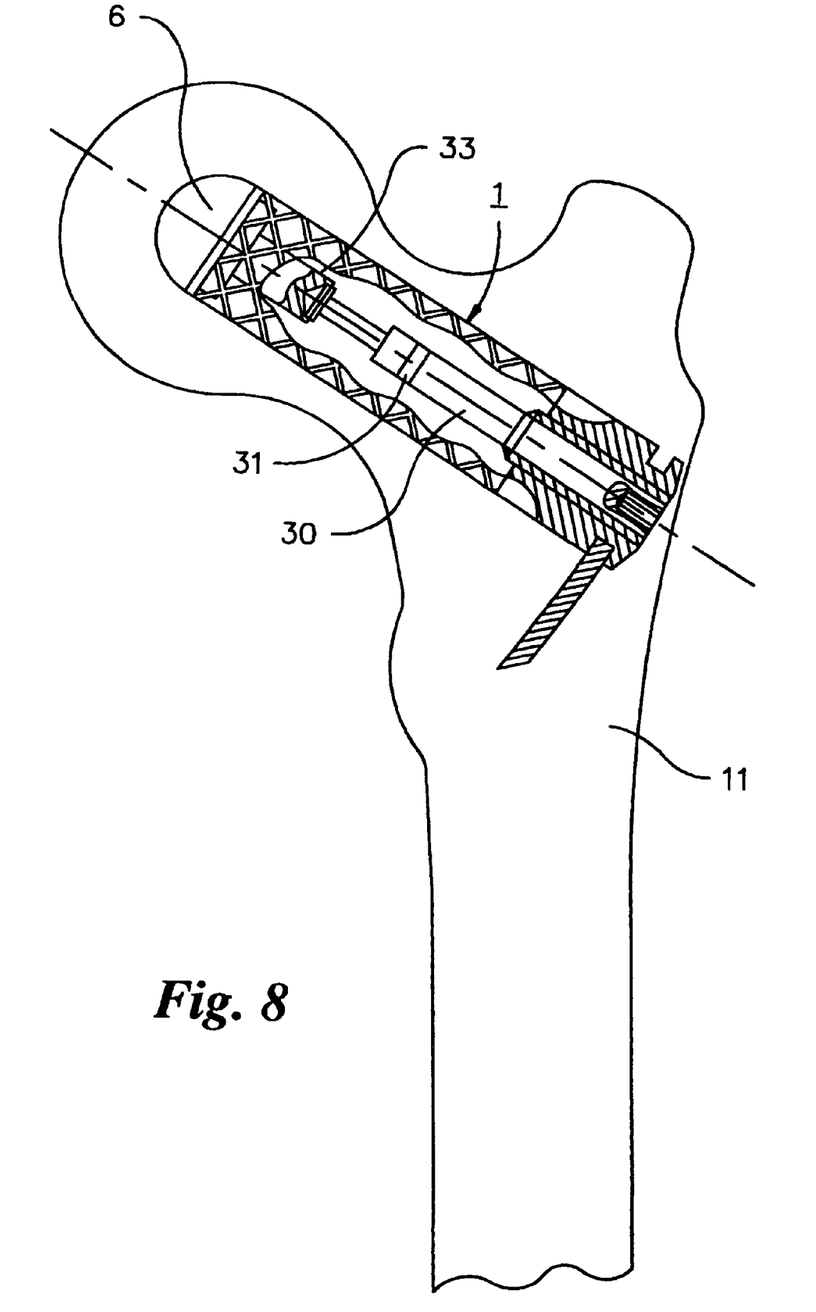
FIG. 8 is a schematic view of the implant position of the implant of FIG. 7 in the femoral neck.
Figure 9:
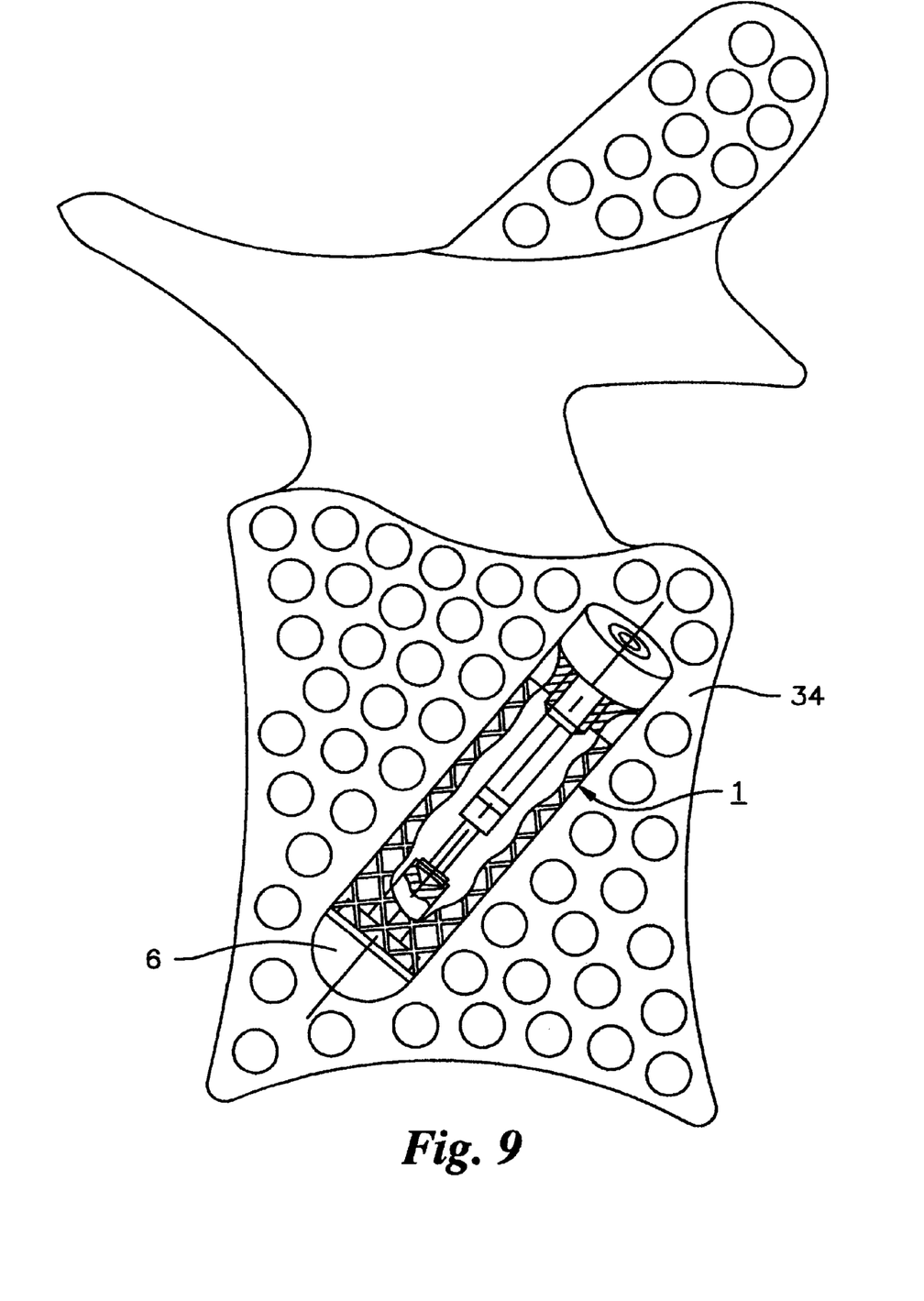
FIG. 9 is a schematic view of the implant position of the implant in a vertebral body.

FIG. 8 shows for completeness of the picture the implanted position of the implant in the femoral neck of the femur 11. A similar embodiment of the reinforcing body 1 can be provided for insertion in a vertebral body 34, as illustrated in FIG. 9. It will be apparent that the dimensions in this case are different from those of the implant which is to be inserted in the femoral neck of a femur.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A method for prophylaxis against fractures of osteoporosis-affected bone segments, comprising the steps of creating a bore in the osteoporosis-affected bone segment, and inserting into the created bore a thin-walled hollow reinforcing body having such a large number of passages in its outer wall that the ratio of the total area of the passages to the total surface area is at least 1:2, such that bone material of the bone segment can grow through the passages into an interior of the reinforcing body.

2. The method of claim 1, wherein the reinforcing body comprises a biocompatible metal, and wherein an open-mesh, three-dimensional spatial network structure is provided at least in sections on its surface.

3. The method of claim 1, wherein the reinforcing body comprises a biocompatible plastic, and wherein the reinforcing body is deformable by a built-in mechanism for application of a pulling force.

4. The method of claim 1, wherein the bore is made in a femur bone neck, and wherein the reinforcing body comprises a substantially cylindrical sleeve, which is distally closed with a convex head member and is proximally closable with a closing piece.

5. The method of claim 4, wherein the convex head member is provided at least partially with a spatial network structure.

6. The method of claim 4, wherein the proximal closing piece is provided at least partially with a spatial network structure.

7. The method of claim 4, wherein a threaded shaft runs in the interior of the sleeve between the head member and the closing piece and is connected to these, the threaded shaft being capable of generating a pulling force upon its rotation.

8. The method of claim 4, wherein a pulling cord is tensioned in the interior of the sleeve between the head member and the closing piece, the pulling cord being further tensionable from outside the sleeve in order to be able to generate a pulling force for deformation of the sleeve.

9. The method of claim 1, wherein the outer wall is coated with an agent resorbable by the patient's body.

10. The method of claim 9, wherein the agent is hydroxylapatite.

11. The method of claim 9, wherein the agent comprises an alpha-tricalcium phosphate ceramic.

12. The method according to claim 1, wherein the bore is made in bone selected from the group consisting of a femur bone neck, a vertebral column and a wrist joint bone.

13. The method of claim 1, wherein an electrical coil is arranged on a magnetic core centrally arranged in the reinforcing body, the electrical coil being activatable from outside the body.

14. The method of claim 13, wherein the magnetic core is constructed as a threaded shaft.

15. The method of claim 13, wherein a head member of the reinforcing body has an extension protruding into the interior of the reinforcing body and has a recess for securing the centered position of the magnetic core.

16. A method for prophylaxis against fractures of osteoporosis-affected bone segments, comprising the steps of creating a bore in the osteoporosis-affected bone segment, and inserting into the created bore a solid implant core forming a reinforcing core for the bone segment, the surface of the solid implant core being provided at least partially with an open-mesh, three-dimensional spatial network structure.

17. The method according to claim 16, wherein the bore is made in bone selected from the group consisting of a femur bone neck, a vertebral column and a wrist joint bone.

18. A method for prophylaxis against fractures of osteoporosis-affected bone segments, comprising the steps of creating a bore in the osteoporosis-affected bone segment, and inserting into the created bore a hollow tube whose outer wall comprises an open-mesh, three-dimensional spatial network structure.

19. The method according to claim 18, wherein the bore is made in bone selected from the group consisting of a femur bone neck, a vertebral column and a wrist joint bone.

20. The method of claim 18, wherein the hollow tube forms a sleeve which is closable with a closing piece on its proximal end, wherein the closing piece also comprises an open-mesh, three-dimensional spatial network structure.

* * * * *